United States Patent
Lee et al.

(10) Patent No.: US 9,822,104 B2
(45) Date of Patent: Nov. 21, 2017

(54) TAXIFOLIN DERIVATIVE WITH SUPERIOR ANTIOXIDANT EFFECT AND COSMETIC COMPOSITION CONTAINING THE SAME

(71) Applicant: Yeomyung Biochem Co., Ltd, Cheongju-si, Chungcheongbuk-do (KR)

(72) Inventors: Jae Duk Lee, Cheongju-si (KR); Hyun Jin An, Jeonju-si (KR); Da Hye Park, Cheongju-si (KR); Yong Sub Yi, Asan-si (KR); Yong Hwa Lee, Asan-si (KR)

(73) Assignee: Yeomyung Biochem Co., Ltd., Cheongju-si (KR)

( * ) Notice: Subject to any disclaimer, the term of this patent is extended or adjusted under 35 U.S.C. 154(b) by 0 days.

(21) Appl. No.: 15/232,238

(22) Filed: Aug. 9, 2016

(65) Prior Publication Data
US 2017/0217944 A1    Aug. 3, 2017

(30) Foreign Application Priority Data
Aug. 24, 2015   (KR) .................. 10-2015-0118820

(51) Int. Cl.
| | | |
|---|---|---|
| *C07D 409/12* | (2006.01) | |
| *A61Q 19/00* | (2006.01) | |
| *A61Q 19/08* | (2006.01) | |
| *A61K 8/49* | (2006.01) | |

(52) U.S. Cl.
CPC .............. *C07D 409/12* (2013.01); *A61K 8/49* (2013.01); *A61Q 19/00* (2013.01); *A61Q 19/08* (2013.01)

(58) Field of Classification Search
CPC ........ C07D 409/12; A61K 8/49; A61Q 19/00; A61Q 19/08

USPC ......................................................... 549/39
See application file for complete search history.

(56) References Cited

U.S. PATENT DOCUMENTS

| | | | | |
|---|---|---|---|---|
| 7,547,729 | B2 * | 6/2009 | Caumont-Bertrand | C07C 59/90 514/557 |
| 2009/0215881 | A1 * | 8/2009 | Delaire ................. | A61K 8/375 514/441 |
| 2010/0234452 | A1 * | 9/2010 | Mian .................... | A61K 31/166 514/440 |

(Continued)

FOREIGN PATENT DOCUMENTS

| | | |
|---|---|---|
| KR | 10-2014-0108797 A | 9/2014 |
| KR | 10-2015-0020466 A | 2/2015 |

(Continued)

OTHER PUBLICATIONS

Chemical Abstracts STN Registry Database record for RN 1883827-78-8 entered on Mar. 21, 2016.*

(Continued)

*Primary Examiner* — Daniel R Carcanague
(74) *Attorney, Agent, or Firm* — Vorys, Sater, Seymour & Pease LLP; Mih Suhn Koh

(57) ABSTRACT

Disclosed are taxifolin derivative with superior antioxidant effect, a method of synthesizing the same and a cosmetic composition containing the same. In accordance with the method, taxifolin derivatives having higher antioxidant activity than taxifolin can be synthesized using lipoic acid. As such, a novel taxifolin derivative synthesized according to the present invention can exhibit anti-aging effects when used for cosmetics and the like.

11 Claims, 16 Drawing Sheets

(56) References Cited

U.S. PATENT DOCUMENTS

2011/0082192 A1\* 4/2011 Milne .................. A61K 31/385
 514/440
2015/0025006 A1\* 1/2015 Laria ...................... A61K 38/26
 514/6.7

FOREIGN PATENT DOCUMENTS

WO WO 2015095968 \* 7/2015
WO WO 2015095970 \* 7/2015

OTHER PUBLICATIONS

Chemical Abstracts STN Registry Database record for RN 1883827-79-9 entered on Mar. 21, 2016.\*
Packer; Free Radical Biology & Medicine, 1995, 19, 227-250.\*
Melagraki; European Journal of Medicinal Chemistry 2009, 44, 3020-3026.\*
Ganceviciene; Dermato-Endocrinology 2012, 4, 308-319.\*
Isaac; Journal of Applied Pharmaceutical Science 2012, 02, 174-179.\*
Kim et al., "Antioxidants and Anti-obesity Activities of Hot Water and Ethanolic Extracts from Cheonnyuncho (*Opuntia humifusa* )", Korean J Food Preserv, vol. 18, No. 3, pp. 366-373, (2011).
Yoon et al., "Total Polyphenol and Flavonoid of Fruit Extract of Opuntia humifusa and Its Inhibitory Effect on the Growth of MCF-7 Human Breast Cancer Cells", J Korean Soc Food Sci Nutr, vol. 38, No. 12, pp. 1679-1684, (2009).

\* cited by examiner 5-(2,2-dimethyl-1,3-dithian-4-yl)pentyl 2,2,2-trichloroacetimidate 1H of 1 in DMSO 1H of 2 in DMSO 1H of 3 in DMSO 1H of 4 in DMSO 7-(5-(1,2-dithiolan-3-yl)pentyloxy)-2-(3,4-dihydroxyphenyl)-3,5-dihydroxychroman-4-one {taxifolin-7-lipoate}

1H of 5 in DMSO 1H of 2 in DMSO 1H of 3 in CDCl3

FIG. 14

TAXIFOLIN DERIVATIVE WITH SUPERIOR ANTIOXIDANT EFFECT AND COSMETIC COMPOSITION CONTAINING THE SAME

BACKGROUND OF THE INVENTION

Field of the Invention

The present invention relates to a taxifolin derivative with superior antioxidant effect, a method of synthesizing the same and a cosmetic composition containing the same.

Description of the Related Art

Most cosmetic materials used in Korea are imported, and the import of cosmetic materials has gradually increased and reached 145 million dollars in 2010. The cosmetic materials are predominantly imported from cosmetic developed countries such as Japan, the United States, Germany and France, and Korea has a high level of dependence on these nations.

As the world has entered the era of limitless competition, alternatives to imported materials, commercialized exports of domestic materials and quality improvement of domestic cosmetics are continuously required to enhance domestic and foreign competitiveness of the domestic cosmetics industry.

Meanwhile, an aging society has triggered active research associated with domestic and foreign skin aging. Skin aging is classified into endogenous aging which naturally occurs due to aging and extrinsic aging which is caused by environmental stress such as UV rays, exhaust and smoking. As aging proceeds, hyper-pigmentation such as blemishes and freckles, degraded elasticity, increased wrinkles and a variety of dermatitis occur on the skin.

Meanwhile, natural substances have long been used as cosmetic materials. In Japan, skin had been cared with rice bran or sponge gourd water and in China, herbs have long been used as cosmetic materials, as disclosed in Oetaebiyo, Cheongeumikbang Cheongeummiyongbang and the like. At present, 272 types of vegetable extracts and 67 types of vegetable oils are disclosed in the Japanese official compendia, "The Cosmetic Ingredient Standards" and "Mix ingredient regulations according to types of cosmetics", and the total 400 or more types of vegetable ingredients including other substances manufacturers independently have an application history are used in cosmetics. In Korea, novel materials containing Chinese or herbal ingredients suitable for woman's skin have been actively developed and commercialized.

Meanwhile, *Opuntia humifusa* (eastern prickly pear) belongs to Cactaceae, which is also called "palm cactus" and have long been used as a food or food alternative. *Opuntia humifusa* can survive in a freezing cold of −20 degrees and can be cultivated for several years to decades. *Opuntia humifusa* has been widely cultivated throughout Korea and has been used as a functional food material.

Research into functions of *Opuntia humifusa* reported that *Opuntia humifusa* has antioxidant and antibacterial effects, effects of alleviating gastric ulcers, protecting liver functions and relieving contact dermatitis, and anti-inflammatory and anti-cancer effects.

PRIOR ART DOCUMENT

Patent Document (Patent Document 1) Korean Patent Laid-open Publication No. 10-2015-0020466 (published on Feb. 26, 2015) discloses an anti-inflammatory composition containing an *Opuntia humifusa* fruit extract as an active ingredient and a health functional food for preventing or relieving inflammation.

(Patent Document 2) Korean Patent Laid-open Publication No. 10-2014-0108797 (published on Sep. 15, 2014) discloses an antioxidant, anti-inflammatory and anti-cancer pharmaceutical composition containing an *Opuntia humifusa* root extract as an active ingredient.

Non-Patent Document (Non-Patent Document 1) Korean. J. Food. Preserv. (18 (3), 366-373 (2011) discloses an ethanol extract which is prepared by stirring a mixture of an *Opuntia humifusa* powder and 80% ethanol at room temperature for 24 hours, followed by extraction, and a hot water extract which is prepared by adding 10 times water to the ground *Opuntia humifusa* extract and extracting the mixture by reflux cooling in a 100° C. water bath for 3 hours while refluxing.

(Non-Patent Document 2) J. Korean. Soc. Food. Sci Nutr (38(12), 1679~1684 (2009)) discloses an extract which is prepared by lyophilizing *Opuntia humifusa* cactus fruits at −70° C., isolating seeds from the product, primarily grinding only the flesh with a disc mill, secondarily grinding the product with a cyclone mill, and extracting the secondarily ground sample in methanol three times at room temperature for 48 to 72 hours, followed by filtration, concentration using a rotary vacuum evaporator, and collection.

SUMMARY OF THE INVENTION

Therefore, the present invention has been made in view of the above problems, and it is an object of the present invention to synthesize a derivative with superior antioxidant activity, based on taxifolin which is a physiologically active substance present in the *Opuntia humifusa* cactus having the functionalities described above, to optimize conditions for the synthesis and thereby develop a cosmetic material containing the derivative.

In accordance with an aspect of the present invention, the above and other objects can be accomplished by the provision of taxifolin-7-lipoate having a structure represented by the following Formula 8 and called "7-(5-(1,2-dithiolan-3-yl)pentyloxy)-2-(3,4-dihydroxyphenyl)-3,5-dihydroxychroman-4-one".

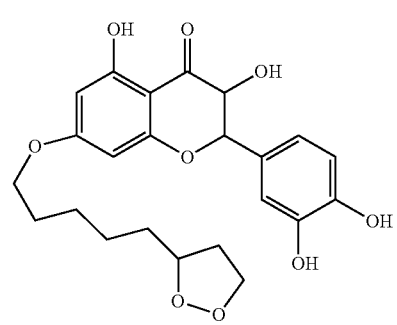

[Formula 8]

In accordance with another aspect of the present invention, provided is taxifolin penta lipoate having a structure represented by the following Formula 10 and called "2-(3,4-bis(5-(1,2-dithiolan-3-yl)pentanoyloxy)phenyl)-4-oxochroman-3,5,7-triyl tris(5-(1,2-dithiolan-3-yl)pentanoate)".

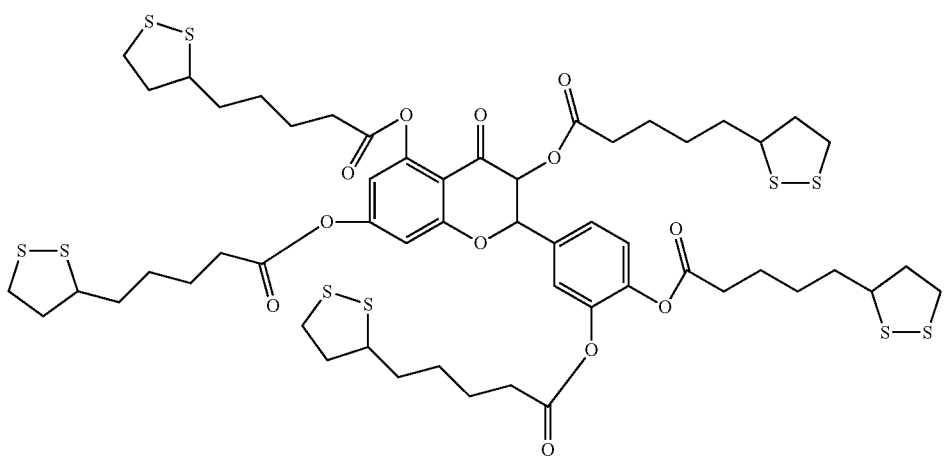

[Formula 10]

In accordance with another aspect of the present invention, provided is a cosmetic composition containing the 7-(5-(1,2-dithiolan-3-yl)pentyloxy)-2-(3,4-dihydroxyphenyl)-3,5-dihydroxychroman-4-one.

In accordance with another aspect of the present invention, provided is a cosmetic composition containing the 2-(3,4-bis(5-(1,2-dithiolan-3-yl)pentanoyloxy)phenyl)-4-oxochroman-3,5,7-triyl tris(5-(1,2-dithiolan-3-yl)pentanoate).

Meanwhile, the cosmetic composition of the present invention may be, for example, used for preventing skin oxidation or aging. This is because the 7-(5-(1,2-dithiolan-3-yl)pentyloxy)-2-(3,4-dihydroxyphenyl)-3,5-dihydroxychroman-4-one and the 2-(3,4-bis(5-(1,2-dithiolan-3-yl)pentanoyloxy)phenyl)-4-oxochroman-3,5,7-triyl tris(5-(1,2-dithiolan-3-yl)pentanoate) have superior antioxidant effects, as can be seen from the test according to the present invention.

In accordance with another aspect of the present invention, provided is a method of synthesizing taxifolin-7-lipoate having a structure represented by the following Formula 8 and called "7-(5-(1,2-dithiolan-3-yl)pentyloxy)-2-(3,4-dihydroxyphenyl)-3,5-dihydroxychroman-4-one" by reacting 5-(2,2-dimethyl-1,3-dithian-4-yl)pentyl 2,2,2-trichloroacetimidate having a structure of the following Formula 4 with 4-(3,5-diacetoxy-7-hydroxy-4-oxochroman-2-yl)-1,2-phenylene diacetate having a structure of following Formula 6.

[Formula 4]

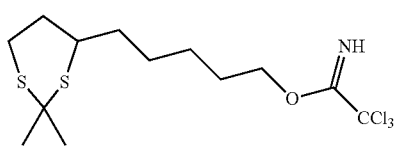

-continued

[Formula 6]

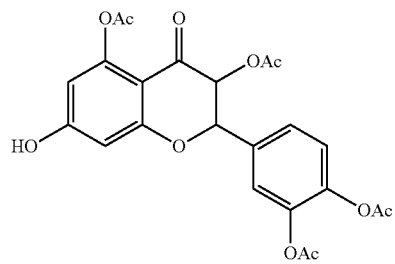

[Formula 8]

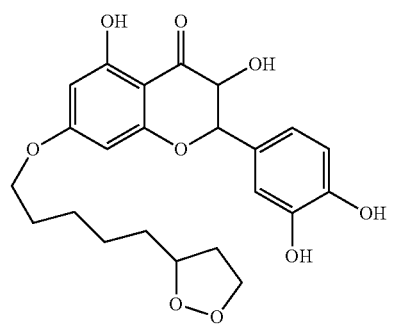

In this case, preferably, the 5-(2,2-dimethyl-1,3-dithian-4-yl)pentyl 2,2,2-trichloroacetimidate is synthesized from lipoic acid as a starting material.

In addition, preferably, the 4-(3,5-diacetoxy-7-hydroxy-4-oxochroman-2-yl)-1,2-phenylene diacetate is synthesized from taxifolin as a starting material.

In accordance with another aspect of the present invention, provided is a method of synthesizing taxifolin penta lipoate by reacting 5-(1,2-dithiolan-3-yl)pentanoyl chloride having a structure of Formula 9 with taxifolin.

[Formula 9]

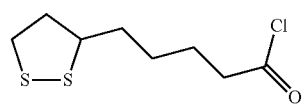

In this case, preferably, the 5-(1,2-dithiolan-3-yl)pentanoyl chloride is synthesized from lipoic acid as a starting material.

BRIEF DESCRIPTION OF THE DRAWINGS

The above and other objects, features and other advantages of the present invention will be more clearly understood from the following detailed description taken in conjunction with the accompanying drawings, in which:

FIG. 14 shows NMR results of synthesized 2-(3,4-bis(5-(1,2-dithiolan-3-yl)pentanoyloxy)phenyl)-4-oxochroman-3,5,7-triyl tris(5-(1,2-dithiolan-3-yl)pentanoate);

DETAILED DESCRIPTION OF THE INVENTION

Lipoic acid used for synthesis of the taxifolin derivative of the present invention is known as a potent and effective antioxidant because it is soluble in both water and lipids. That is, lipoic acid is soluble in blood and other serums due to water-solubility and is also soluble in lipids due to lipid-solubility. Owing to such a property, lipoic acid is known as an ideal antioxidant.

Due to this property, lipoic acid can prevent damage to active oxygen in all cells of all organs including cerebrospinal fluid, blood, depot fat, heart, pancreas, kidney, bones, cartilage and liver. In addition, like vitamin C, lipoic acid plays the same roles in liquids of cells contacting human tissues, blood and other aqueous solutions. Owing to these potent characteristics, lipoic acid can easily pass through a brain-blood barrier and thus can improve brain energy.

Lipoic acid also has the capacity to regenerate other antioxidant agents such as vitamin C, vitamin E and glutathione. If the antioxidant agents exhaust their activities in human body, lipoic acid regenerates the antioxidant agents so that they can function. Accordingly, lipoic acid is also called "antioxidant agent of an antioxidant agent". In addition, lipoic acid prevents cross-linking of collagen in skin and thus wrinkling, enhances whitening effect and finally prevents physical aging.

The present inventors found that taxifolin derivatives, which were synthesized based on lipoic acid having the characteristics described above and taxifolin extracted from *Opuntia humifusa* stems, exhibited excellent antioxidant activity. Based on this finding, the present invention has been completed.

Hereinafter, the present invention will be described in more detail with reference to the following examples, and the scope of the present invention is not limited to the examples and includes variations of technical concepts equivalent thereto.

Example 1: Synthesis of taxifolin-7-lipoate (dihydroguercetin-7-lipoate)

In this Example, taxifolin-7-lipoate (taxifolin derivative) also called "dihydroquercetin-7-lipoate" was synthesized. The dihydroquercetin-7-lipoate was synthesized by three steps, i.e., (1) preparation of the intermediate, 5-(2,2-dimethyl-1,3-dithian-4-yl)pentyl 2,2,2-trichloroacetimidate, (2) preparation of the intermediate, 4-(3,5-diacetoxy-7-hydroxy-4-oxochroman-2-yl)-1,2-phenylene diacetate, and (3) preparation of the final product, dihydroquercetin-7-lipoate.

Figure 1:
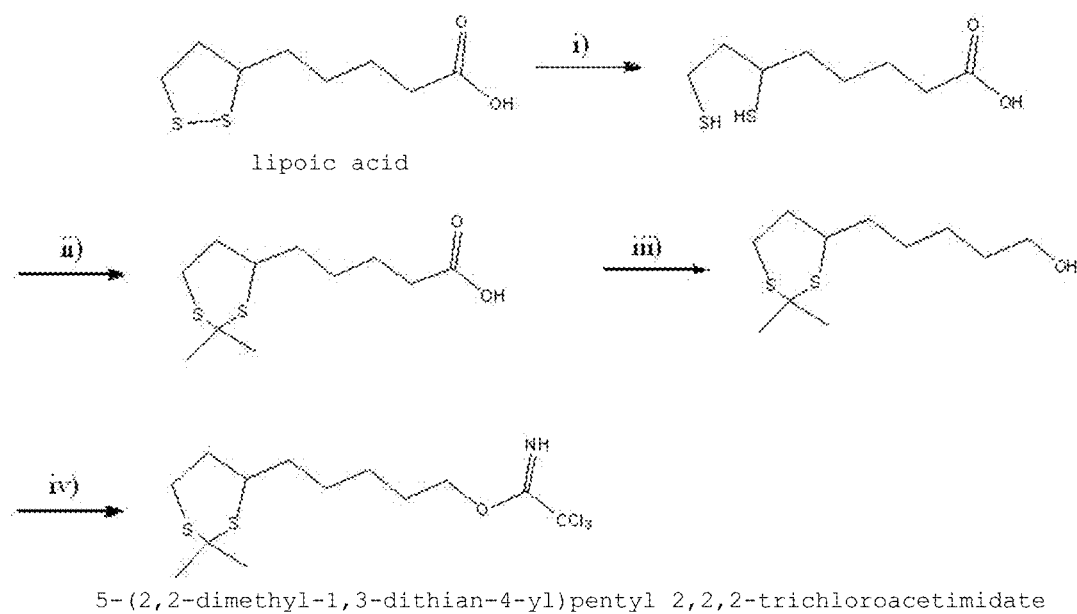
FIG. 1 shows a process of synthesizing 5-(2,2-dimethyl-1,3-dithian-4-yl)pentyl 2,2,2-trichloroacetimidate as an intermediate from lipoic acid.

(1) Synthesis of intermediate, 5-(2,2-dimethyl-1,3-dithian-4-yl)pentyl 2,2,2-trichloroacetimidate 5-(2,2-dimethyl-1,3-dithian-4-yl)pentyl 2,2,2-trichloroacetimidate was prepared from lipoic acid as a starting material. The preparation was conducted by the process as shown in FIG. 1. FIG. 1 shows a process of synthesizing 5-(2,2-dimethyl-1,3-dithian-4-yl)pentyl 2,2,2-trichloroacetimidate as an intermediate from lipoic acid. As shown in FIG. 1, 5-(2,2-dimethyl-1,3-dithian-4-yl)pentyl 2,2,2-trichloroacetimidate was synthesized from lipoic acid by a total of four steps. Hereinafter, this process will be described in detail.

i) Preparation of 6,8-dimercaptooctanoic acid having a structure of Formula 1

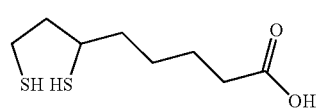

[Formula 1]

Figure 2:
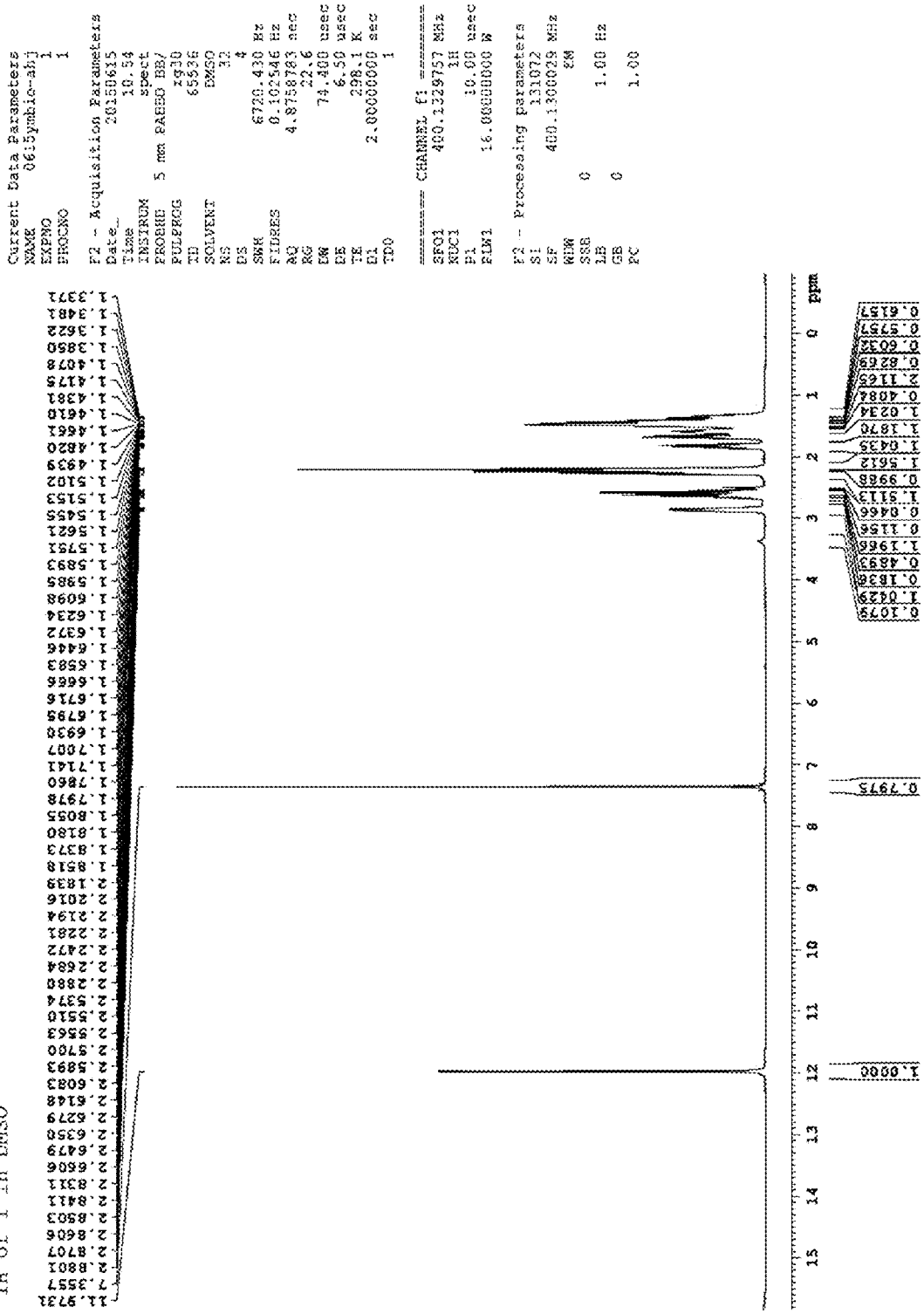
FIG. 2 shows NMR results of synthesized 6,8-dimercaptooctanoic acid.

Lipoic acid (12.2 g, 59 mmol) was dissolved in 250 ml of 0.25M NaHCO$_3$ and cooled to 0° C. Then, sodium borohydride (9.0 g, 238 mmol) was slowly added to the resulting solution while maintaining the temperature at 4° C. or less. After further stirring at the same temperature for 2 hours, the reaction solution was acidified with 6M HCl (pH 1). Then, the resulting product was extracted in 75 ml of toluene. This step was repeated three times. The organic layer was dehydrated with MgSO$_4$ and then filtered, and the resulting filtrate was concentrated under reduced pressure. As a result of this step, 6,8-dimercaptooctanoic acid (8.89 g, 72%) was obtained as a clear oil (FIG. 2). FIG. 2 shows NMR results of synthesized 6,8-dimercaptooctanoic acid.

ii) Preparation of 5-(2,2-dimethyl-1,3-dithian-4-yl)pentanoic acid having a structure of Formula 2

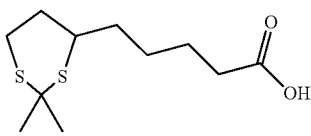

[Formula 2]

Figure 3:
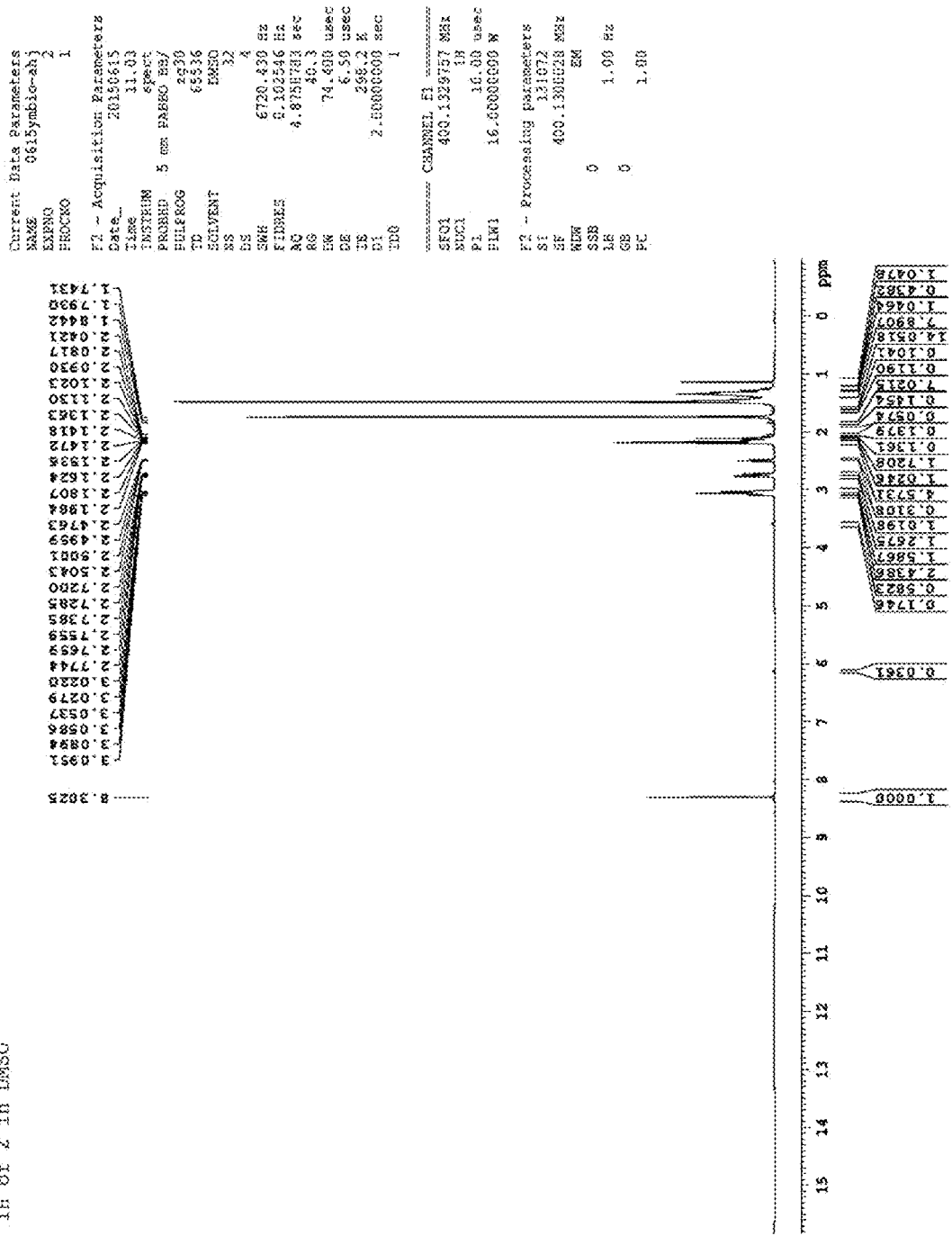
FIG. 3 shows NMR results of synthesized 5-(2,2-dimethyl-1,3-dithian-4-yl)pentanoic acid.

6,8-dimercaptooctanoic acid (6 g, 28.8 mmol) was dissolved in acetone (120 ml), BF$_3$OEt$_2$ (0.55 ml) was added thereto, and the resulting mixture was refluxed at 60° C. and stirred for 15 hours or longer. The solvent was concentrated under reduced pressure and the residue was dissolved in chloroform (160 ml). The resulting solution was washed with 1M NaOH and the solvent was removed by concentration under reduced pressure. As a result of this step, 5-(2,2-dimethyl-1,3-dithian-4-yl)pentanoic acid (4.52 g, 75%) was obtained as a light yellow oil. FIG. 3 shows NMR results of synthesized 5-(2,2-dimethyl-1,3-dithian-4-yl)pentanoic acid.

iii) Preparation of 5-(2,2-dimethyl-1,3-dithian-4-yl)pentan-1-ol having a structure of Formula 3

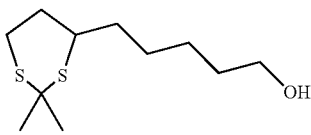

[Formula 3]

Figure 4:
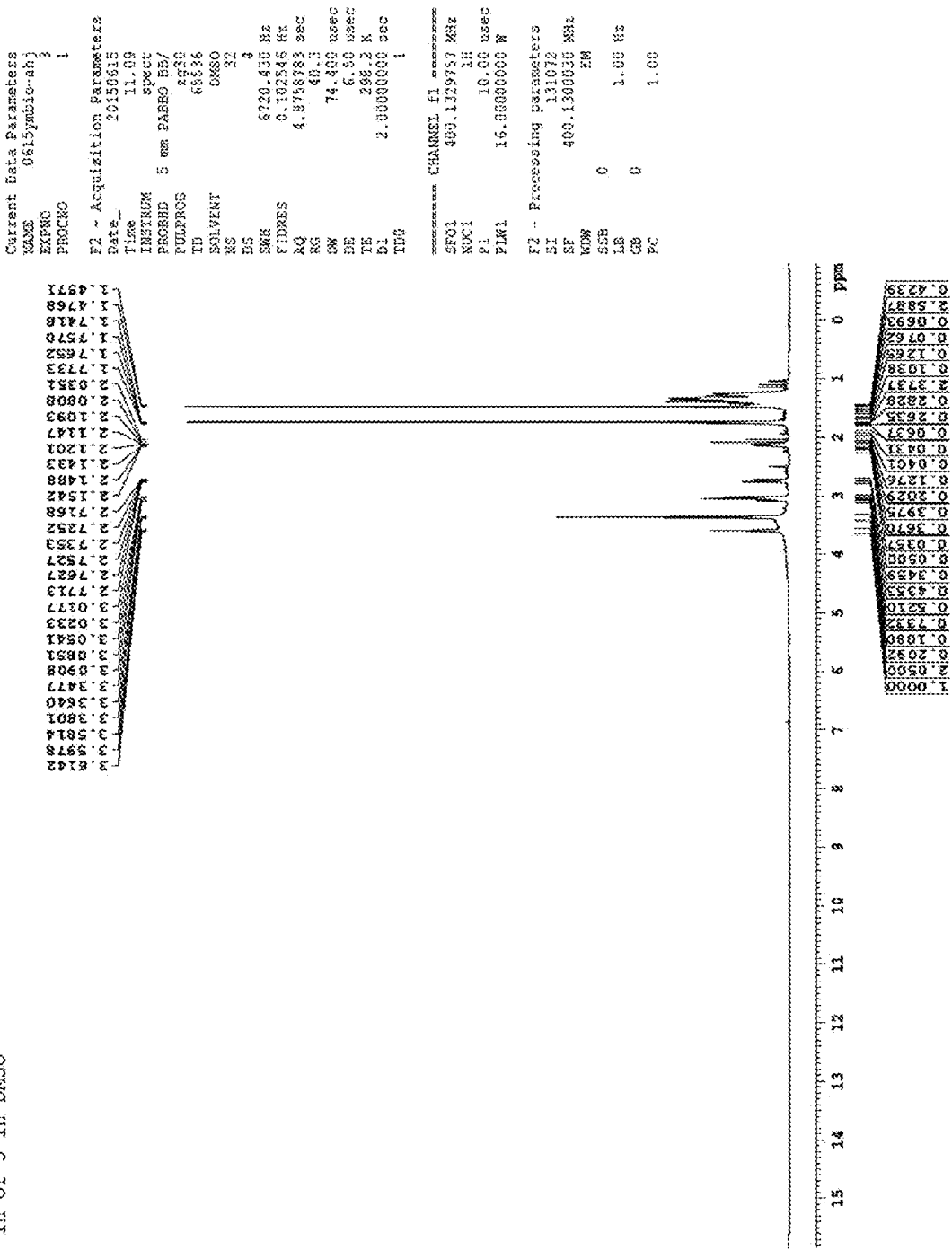
FIG. 4 shows NMR results of synthesized 5-(2,2-dimethyl-1,3-dithian-4-yl)pentan-1-ol.

5-(2,2-dimethyl-1,3-dithian-4-yl)pentanoic acid (3 g, 12.08 mmol) was dissolved in THF (30 ml). Lithium aluminum hydride (0.92 g, 24.16 mmol) was dissolved in 30 ml of THF. Then, the two solutions were mixed and reacted under reflux cooling for one hour. Then, the reaction solution was cooled to room temperature, acidified with 15 ml of 10% HCl and extracted with ether (60 ml). This step was repeated three times in total. The ether layer was washed with distilled water. The residue was dehydrated with MgSO$_4$ and then filtered and the solvent was concentrated under reduced pressure. As a result of this step, 5-(2,2-dimethyl-1,3-dithian-4-yl)pentan-1-ol (2.64 g, 88%) was obtained as a white oil. FIG. 4 shows NMR results of synthesized 5-(2,2-dimethyl-1,3-dithian-4-yl)pentan-1-ol.

iv) Preparation of 5-(2,2-dimethyl-1,3-dithian-4-yl)pentyl 2,2,2-trichloroacetimidate having a structure of Formula 4

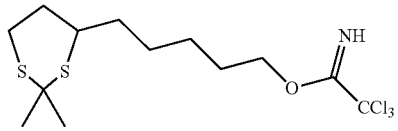

[Formula 4]

Figure 5:
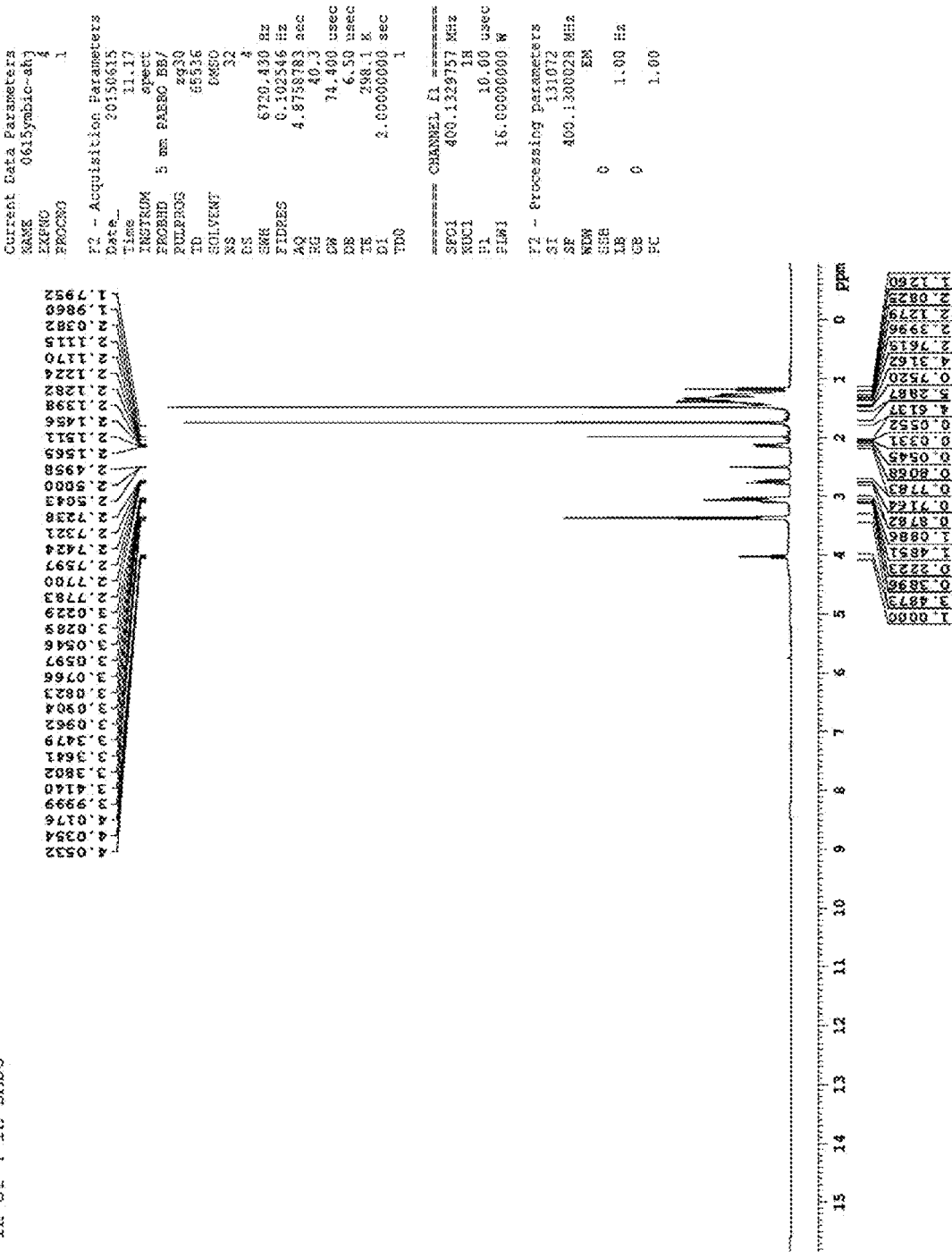
FIG. 5 shows NMR results of synthesized 5-(2,2-dimethyl-1,3-dithian-4-yl)pentyl 2,2,2-trichloroacetimidate.

5-(2,2-dimethyl-1,3-dithian-4-yl)pentan-1-ol (2.22 g, 9.47 mmol) was dissolved in dichloromethane (20 ml), and cesium carbonate (0.6 g, 1.85 mmol) and trichloroacetonitrile (5.7 ml, 56.82 mmol) were added thereto and the resulting solution was stirred at room temperature for three hours. Then, the reaction solution was filtered and concentrated under reduced pressure. Then, the concentrate was purified by column chromatography (hexane:ethyl acetate=2:1) to obtain 5-(2,2-dimethyl-1,3-dithian-4-yl)pentyl 2,2,2-trichloroacetimidate (1.6 g, 44%) as a clear oil. FIG. 5 shows NMR results of synthesized 5-(2,2-dimethyl-1,3-dithian-4-yl)pentyl 2,2,2-trichloroacetimidate.

Figure 6:
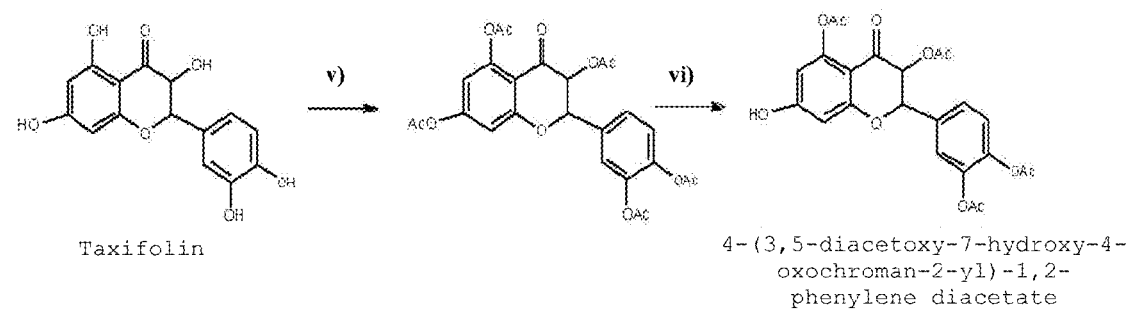
FIG. 6 shows a process of synthesizing the intermediate, 4-(3,5-diacetoxy-7-hydroxy-4-oxochroman-2-yl)-1,2-phenylene diacetate.

(2) Preparation of the Intermediate, 4-(3,5-diacetoxy-7-hydroxy-4-oxochroman-2-yl)-1,2-phenylene diacetate The intermediate, 4-(3,5-diacetoxy-7-hydroxy-4-oxochroman-2-yl)-1,2-phenylene diacetate was synthesized by steps v) to vi) shown in FIG. 6. FIG. 6 shows a process of synthesizing the intermediate, 4-(3,5-diacetoxy-7-hydroxy-4-oxochroman-2-yl)-1,2-phenylene diacetate.

v) Preparation of 2-(3,4-diacetoxyphenyl)-4-oxochroman-3,5,7-triyl triacetate having a structure of Formula 5

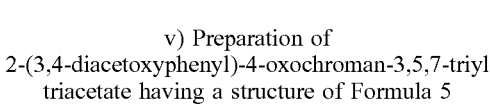

[Formula 5]

Figure 7:
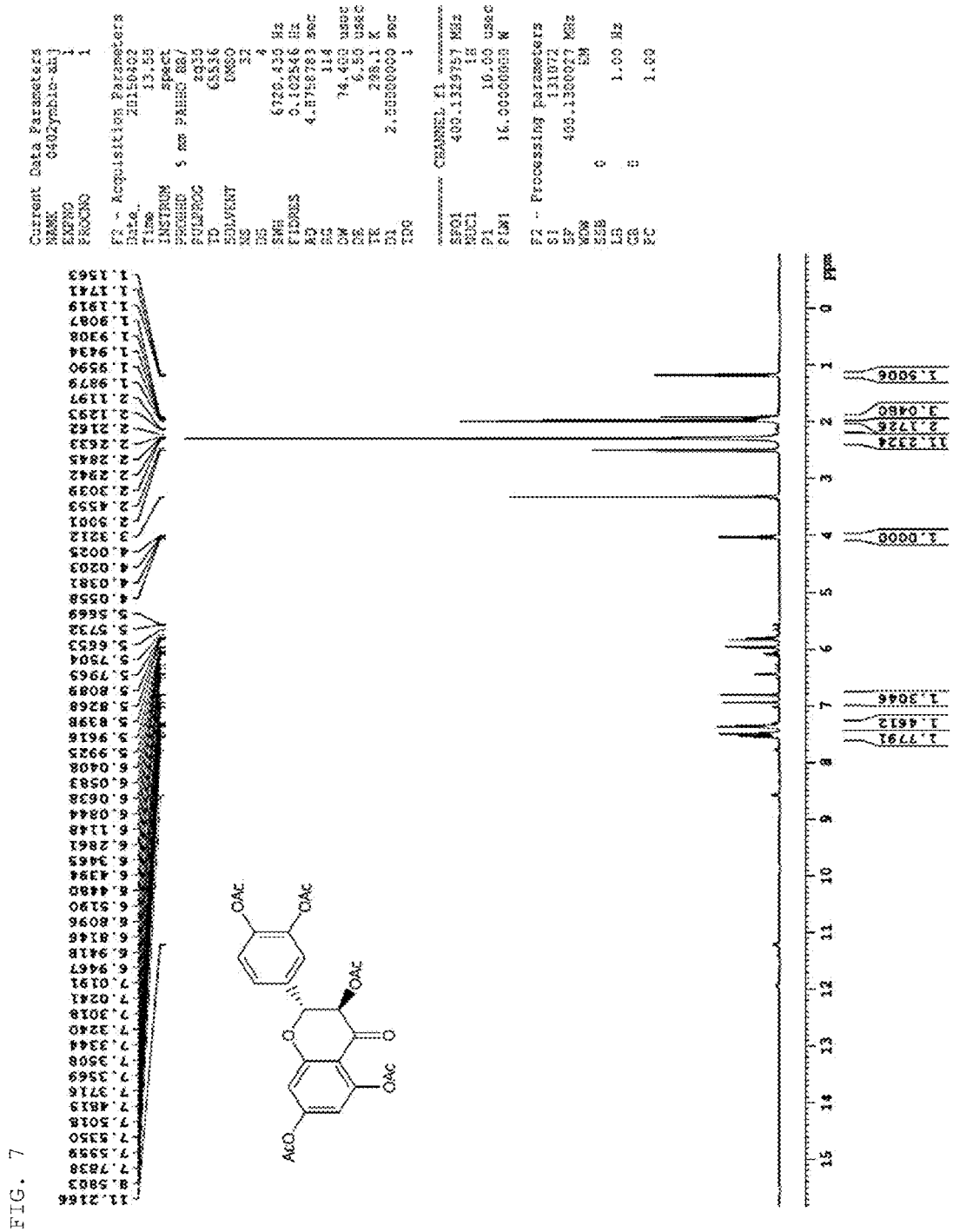
FIG. 7 shows NMR results of synthesized 2-(3,4-diacetoxyphenyl)-4-oxochroman-3,5,7-triyl triacetate.

Taxifolin (5 g, 16.4 mmol) was dissolved in anhydrous pyridine (40 ml) and acetic anhydride (12.38 ml, 131.2 mmol) was added thereto. The resulting mixture was stirred at room temperature for 15 hours. Then, the reaction product was concentrated under reduced pressure to obtain 2-(3,4-diacetoxyphenyl)-4-oxochroman-3,5,7-triyl triacetate (8.43 g) as a brown gel. FIG. 7 shows NMR results of synthesized 2-(3,4-diacetoxyphenyl)-4-oxochroman-3,5,7-triyl triacetate.

vi) Preparation of 4-(3,5-diacetoxy-7-hydroxy-4-oxochroman-2-yl)-1,2-phenylene diacetate having a structure of Formula 6

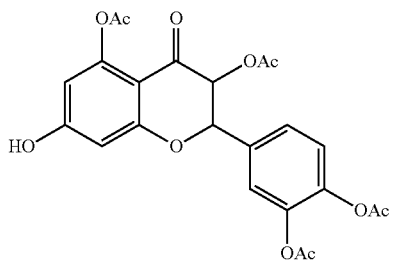

[Formula 6]

Figure 8:
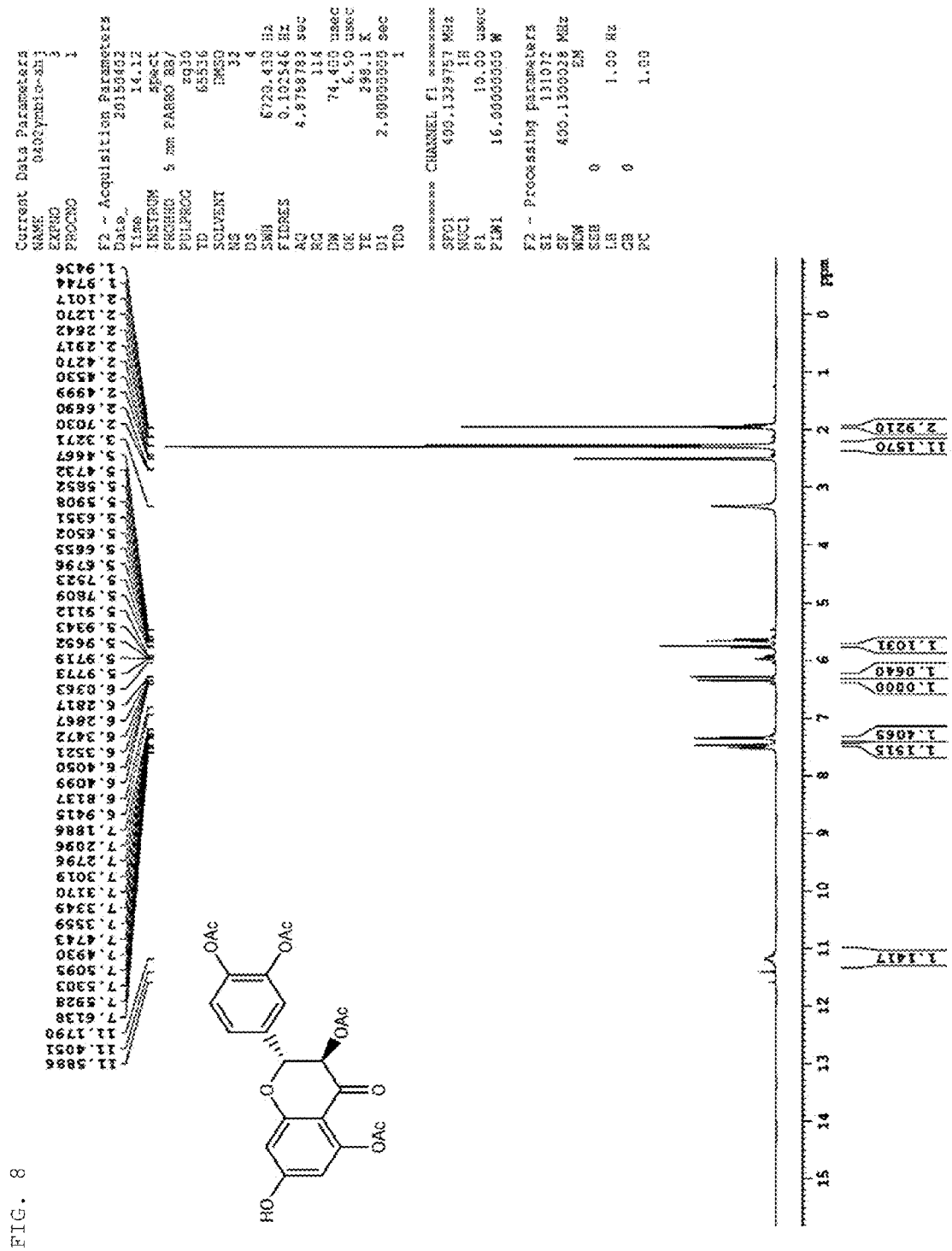
FIG. 8 shows NMR results of synthesized 4-(3,5-diacetoxy-7-hydroxy-4-oxochroman-2-yl)-1,2-phenylene diacetate.

2-(3,4-diacetoxyphenyl)-4-oxochroman-3,5,7-triyl triacetate (9.14 g, 17.8 mmol) was dissolved in 1-methyl-2-pyrrolidone (42 ml). Imidazole (242 mg, 3.55 mmol) and thiophenol (1.5 ml, 15 mmol) were added at 0° C. to the solution and the resulting mixture was stirred at room temperature for three hours. Dichloromethane was added to the reaction product and the mixture was washed with a 1M aqueous hydrochloric acid solution. The organic layer was concentrated under reduced pressure and purified by silica gel column chromatography (dichloromethane:methanol=30:1) to obtain 4-(3,5-diacetoxy-7-hydroxy-4-oxochroman-2-yl)-1,2-phenylene diacetate (5 g, 59%) as a light brown gel. FIG. 8 shows NMR results of synthesized 4-(3,5-diacetoxy-7-hydroxy-4-oxochroman-2-yl)-1,2-phenylene diacetate.

Figure 9:
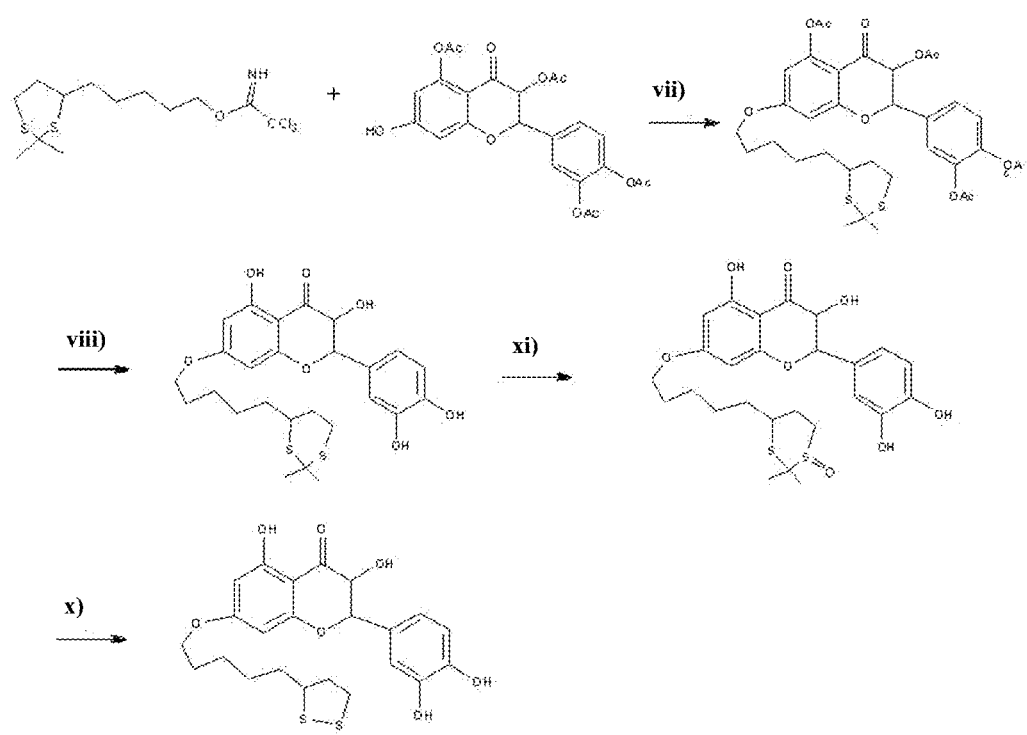
FIG. 9 shows a process of synthesizing 7-(5-(1,2-dithiolan-3-yl)pentyloxy)-2-(3,4-dihydroxyphenyl)-3,5-dihydroxychroman-4-one.

(3) Preparation of 7-(5-(1,2-dithiolan-3-yl)pentyloxy)-2-(3,4-dihydroxyphenyl)-3,5-dihydroxychroman-4-one 7-(5-(1,2-dithiolan-3-yl)pentyloxy)-2-(3,4-dihydroxyphenyl)-3,5-dihydroxychroman-4-one was synthesized from the previously synthesized intermediate, 5-(2,2-dimethyl-1,3-dithian-4-yl)pentyl 2,2,2-trichloroacetimidate as above and the intermediate, 4-(3,5-diacetoxy-7-hydroxy-4-oxochroman-2-yl)-1,2-phenylene diacetate by the process shown in FIG. 9. FIG. 9 shows a process of synthesizing 7-(5-(1,2-dithiolan-3-yl)pentyloxy)-2-(3,4-dihydroxyphenyl)-3,5-dihydroxychroman-4-one.

vii) Preparation of 4-(3,5-diacetoxy-7-(5-(2,2-dimethyl-1,3-dithian-4-yl)pentyloxy)-4-oxochroman-2-yl)-1,2-phenylene diacetate having a structure of Formula 7

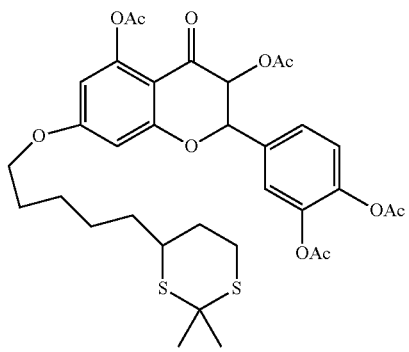

[Formula 7]

Figure 10:
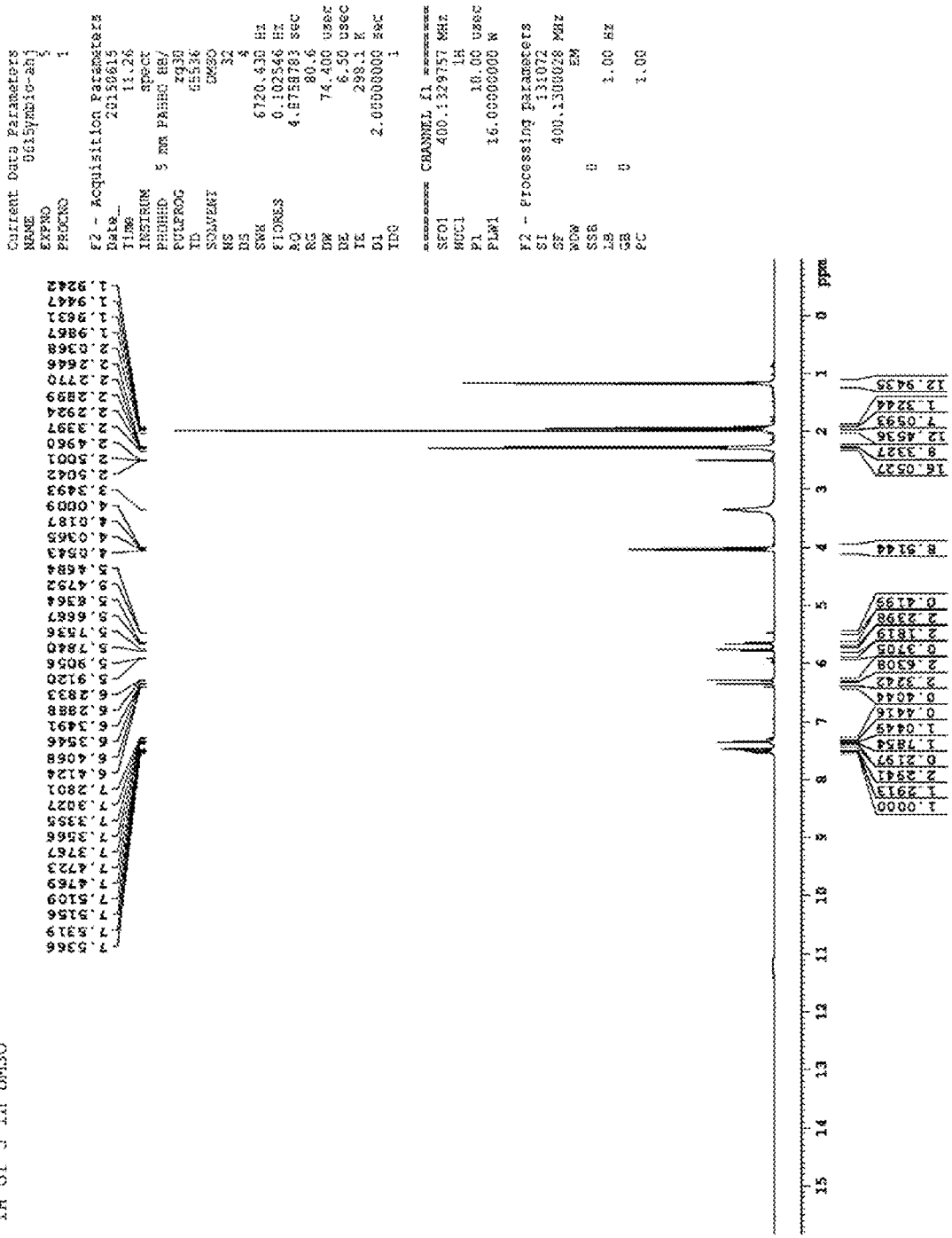
FIG. 10 shows NMR results of synthesized 4-(3,5-diacetoxy-7-(5-(2,2-dimethyl-1,3-dithian-4-yl)pentyloxy)-4-oxochroman-2-yl)-1,2-phenylene diacetate.

4-(3,5-diacetoxy-7-hydroxy-4-oxochroman-2-yl)-1,2-phenylene diacetate (0.59 g, 1.25 mmol) and 5-(2,2-dimethyl-1,3-dithian-4-yl)pentyl 2,2,2-trichloroacetimidate (0.71 g, 1.875 mmol) were dissolved in dichloromethane (30 ml). Then, BF$_3$/Et$_2$O (0.17 ml, 1.25 mmol) was added to the solution and the resulting mixture was stirred at room temperature for 15 hours. The reaction product was neutralized with triethylamine and then filtered. The filtrate was concentrated under reduced pressure and purified by silica gel column chromatography (hexane:ethyl acetate=1:1) to obtain 4-(3,5-diacetoxy-7-(5-(2,2-dimethyl-1,3-dithian-4-yl)pentyloxy)-4-oxochroman-2-yl)-1,2-phenylene diacetate (0.23 g, 27%) as a clear oil. FIG. 10 shows NMR results of synthesized 4-(3,5-diacetoxy-7-(5-(2,2-dimethyl-1,3-dithian-4-yl)pentyloxy)-4-oxochroman-2-yl)-1,2-phenylene diacetate.

viii~X) Preparation of 7-(5-(1,2-dithiolan-3-yl)pentyloxy)-2-(3,4-dihydroxyphenyl)-3,5-dihydroxychroman-4-one having a structure of Formula 8

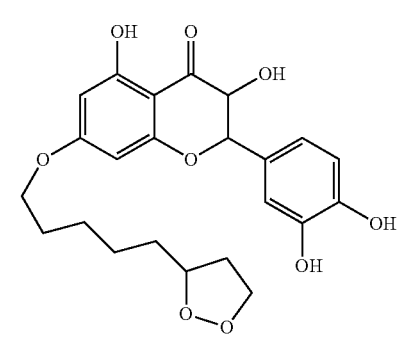

[Formula 8]

A 2M ammonia methanol solution (79 ml) was added to 4-(3,5-diacetoxy-7-(5-(2,2-dimethyl-1,3-dithian-4-yl)pentyloxy)-4-oxochroman-2-yl)-1,2-phenylene diacetate (1.19 g, 1.72 mmol). Then, the resulting mixture was stirred at 0° C. for three hours. The reaction product was concentrated under reduced pressure to obtain 2-(3,4-dihydroxyphenyl)-7-(5-(2,2-dimethyl-1,3-dithian-4-yl)pentyloxy)-3,5-dihydroxychroman-4-one (1.11 g) {viii) reaction}.

2-(3,4-dihydroxyphenyl)-7-(5-(2,2-dimethyl-1,3-dithian-4-yl)pentyloxy)-3,5-dihydroxychroman-4-one (0.63 g, 1.21 mmol) was dissolved in 7 ml of MeOH. Phosphate buffer (2.1 ml, pH 7.2) was dissolved in MeOH (28 ml), the solutions were mixed and sodium periodate (0.24 g, 1.21 mmol) was added thereto. Then, the resulting mixture was stirred at room temperature for 4 days. After 4 days, MC (30 ml) was added to the reaction product and distilled water (20 ml) was then added thereto. Then, the mixture was extracted in MC (20 ml) three times. The extracted organic layer was collected and washed with distilled water and 20 ml of 20% sodium methanesulfonate. The organic layer was dehydrated with MgSO₄ and then filtered. The filtrate was concentrated under reduced pressure. As a result, a reaction product (0.17 g) was obtained {ix)}.

0.42 ml of acetyl chloride was added at 0° C. to (3 ml) of MeOH to prepare a 2M methanolic HCl solution. The reaction product (0.12 g, 0.224 mmol) was added to 25 ml of the methanolic HCl. The resulting mixture was stirred at room temperature for 4 days. After the reaction, the solvent was concentrated under reduced pressure such that the volume of solvent reached about ⅓. 5 mL of water was added to the concentrate and the mixture was extracted in 30 ml of MC. The organic layer was washed with an aqueous 10% Na₂CO₃ solution (10 ml) and then washed with an aqueous 20% sodium methanesulfonate solution. Then, the residue was dehydrated with MgSO₄ and then filtered. The filtrate was concentrated under reduced pressure to obtain 7-(5-(1,2-dithiolan-3-yl)pentyloxy)-2-(3,4-dihydroxyphenyl)-3,5-dihydroxychroman-4-one (40 mg) {x) reaction}.

Figure 11:
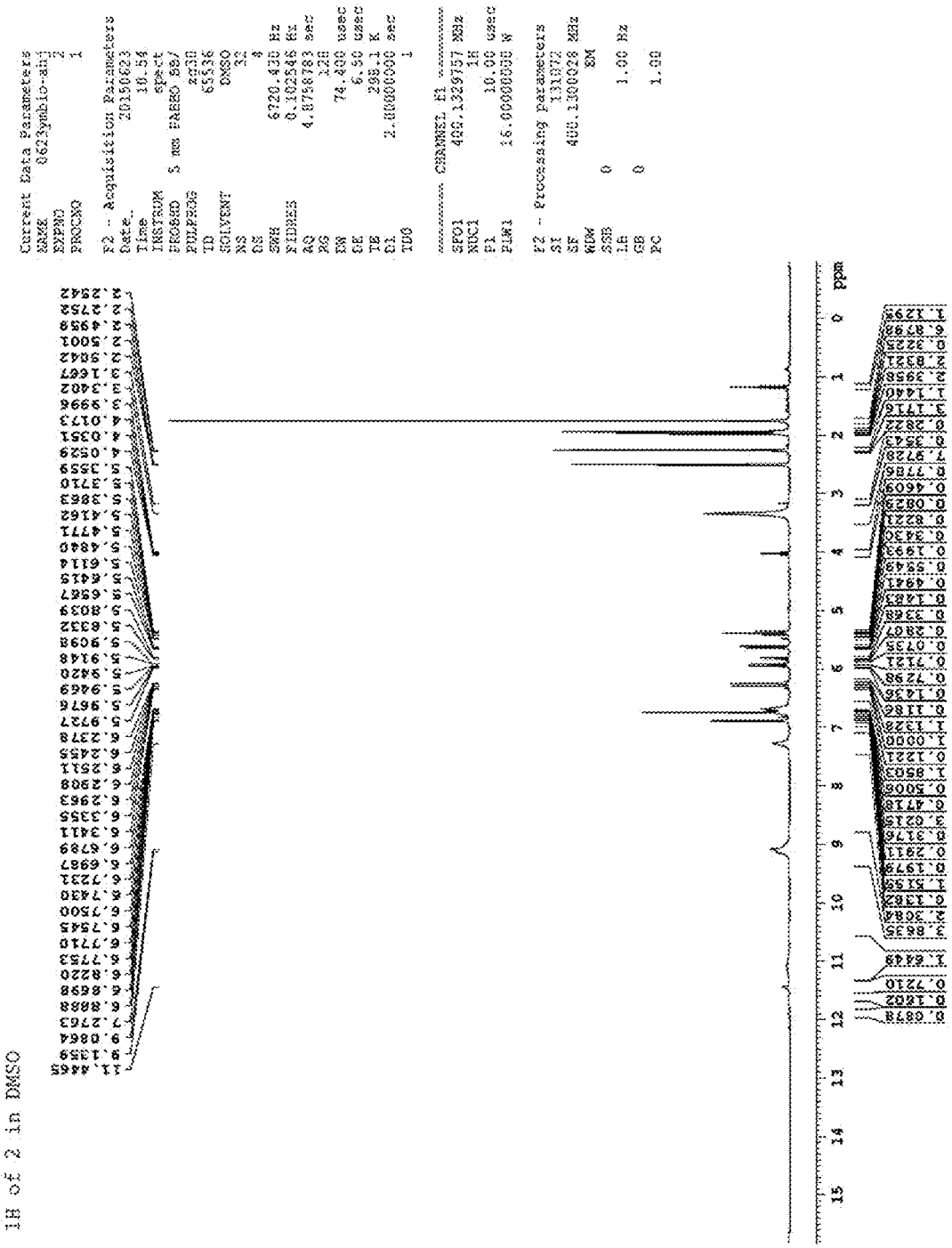
FIG. 11 shows NMR results of synthesized 7-(5-(1,2-dithiolan-3-yl)pentyloxy)-2-(3,4-dihydroxyphenyl)-3,5-dihydroxychroman-4-one.

FIG. 11 shows NMR results of synthesized 7-(5-(1,2-dithiolan-3-yl)pentyloxy)-2-(3,4-dihydroxyphenyl)-3,5-dihydroxychroman-4-one.

Example 2: Synthesis of Taxifolin Penta Lipoate

Figure 12:
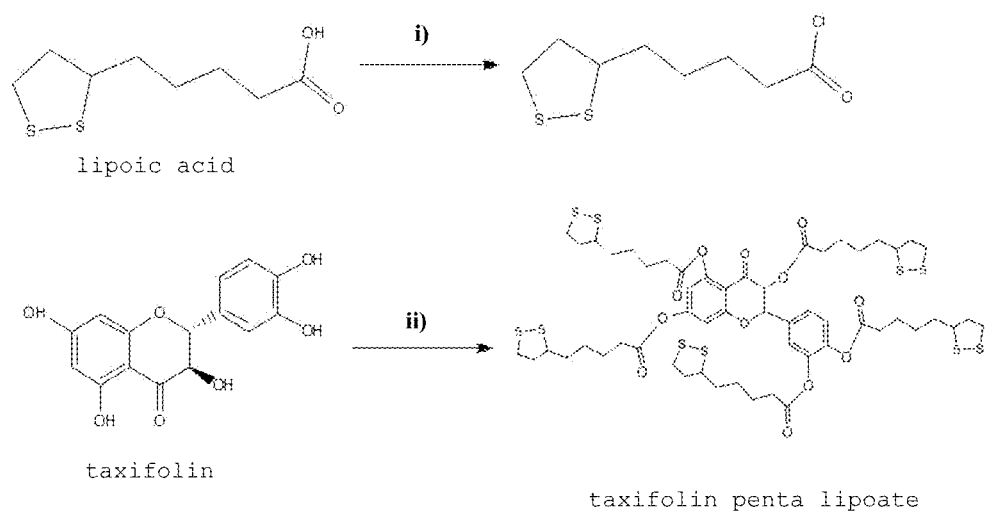
FIG. 12 shows a process of synthesizing taxifolin penta lipoate.

In this Example, taxifolin penta lipoate was synthesized by the process shown in FIG. 12. FIG. 12 shows a process of synthesizing taxifolin penta lipoate.

i) Preparation of 5-(1,2-dithiolan-3-yl)pentanoyl chloride having a structure of Formula 9

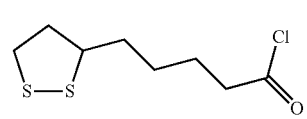

[Formula 9]

Figure 13:
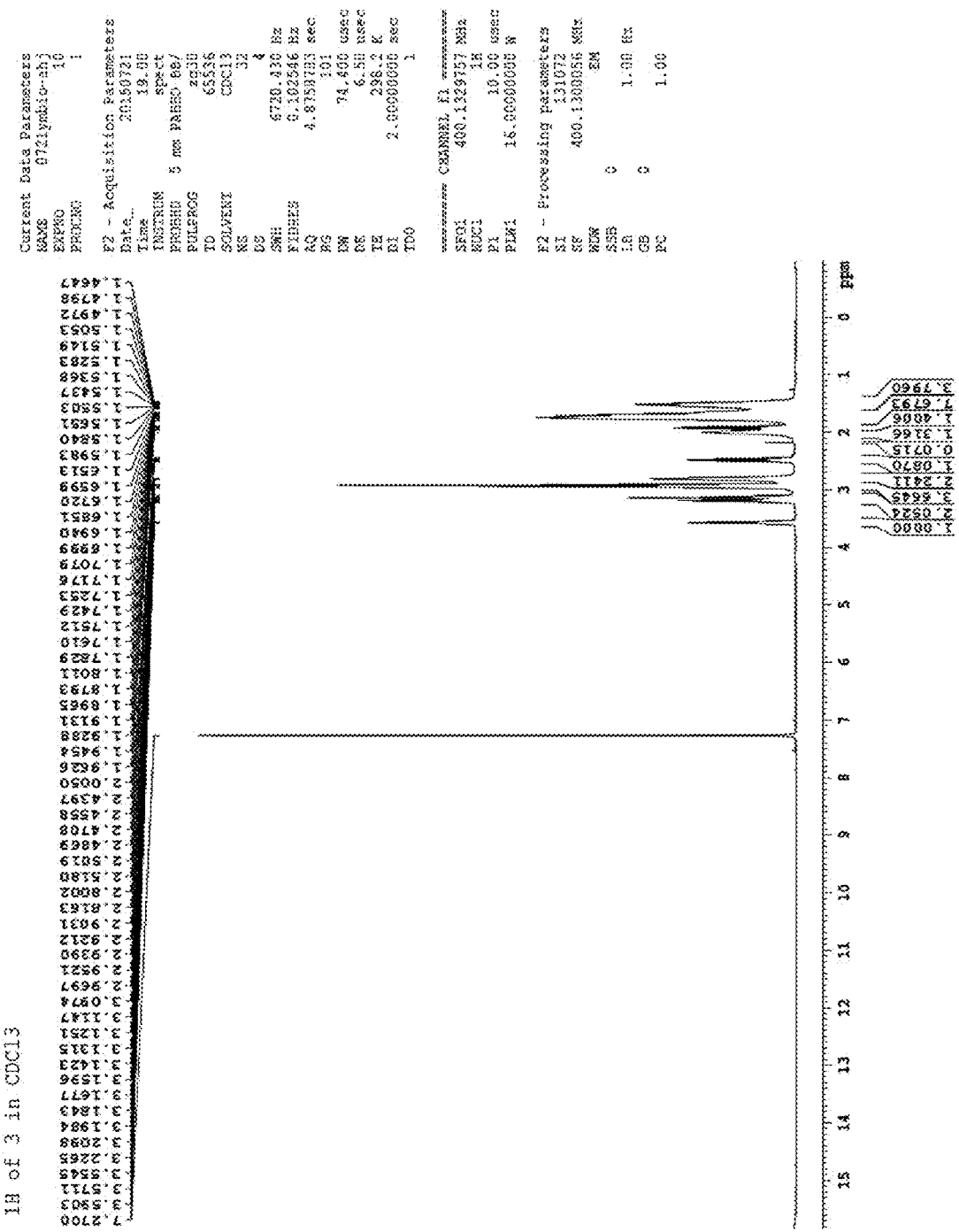
FIG. 13 shows NMR results of synthesized 5-(1,2-dithiolan-3-yl)pentanoyl chloride.

Thionyl chloride (5.27 ml, 72.70 mmol) was dissolved at 0° C. in 300 ml of MC. Lipoic acid (10 g, 48.47 mmol) was dissolved in MC 200 ml to separately prepare a lipoic acid solution. The lipoic acid solution was dropwise added to the thionyl chloride solution over one hour and stirred at 0° C. for 3 hours and the solvent was concentrated under reduced pressure at room temperature. As a result of the aforementioned step, 5-(1,2-dithiolan-3-yl)pentanoyl chloride (18 g) was obtained as a brown gel. FIG. 13 shows NMR results of synthesized 5-(1,2-dithiolan-3-yl)pentanoyl chloride.

ii) Preparation of 2-(3,4-bis(5-(1,2-dithiolan-3-yl)pentanoyloxy)phenyl)-4-oxochroman-3,5,7-triyl tris (5-(1,2-dithiolan-3-yl)pentanoate) having a structure of Formula 10

[Formula 10]

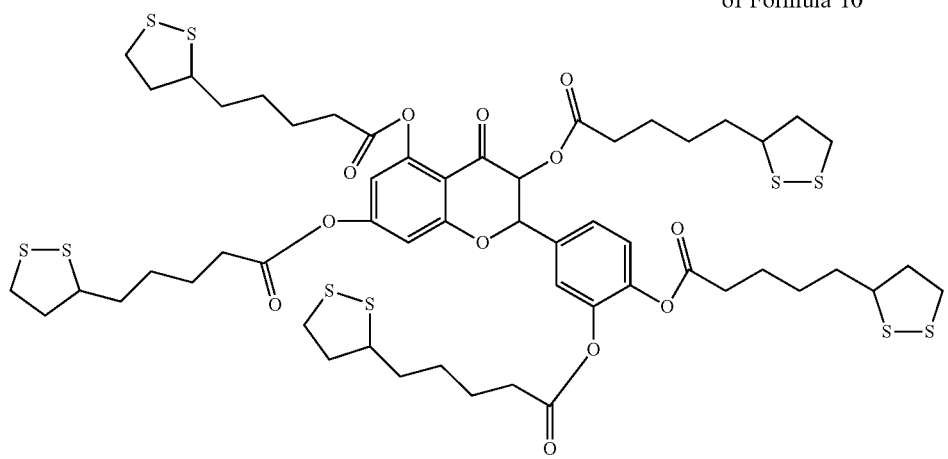

Figure 14:
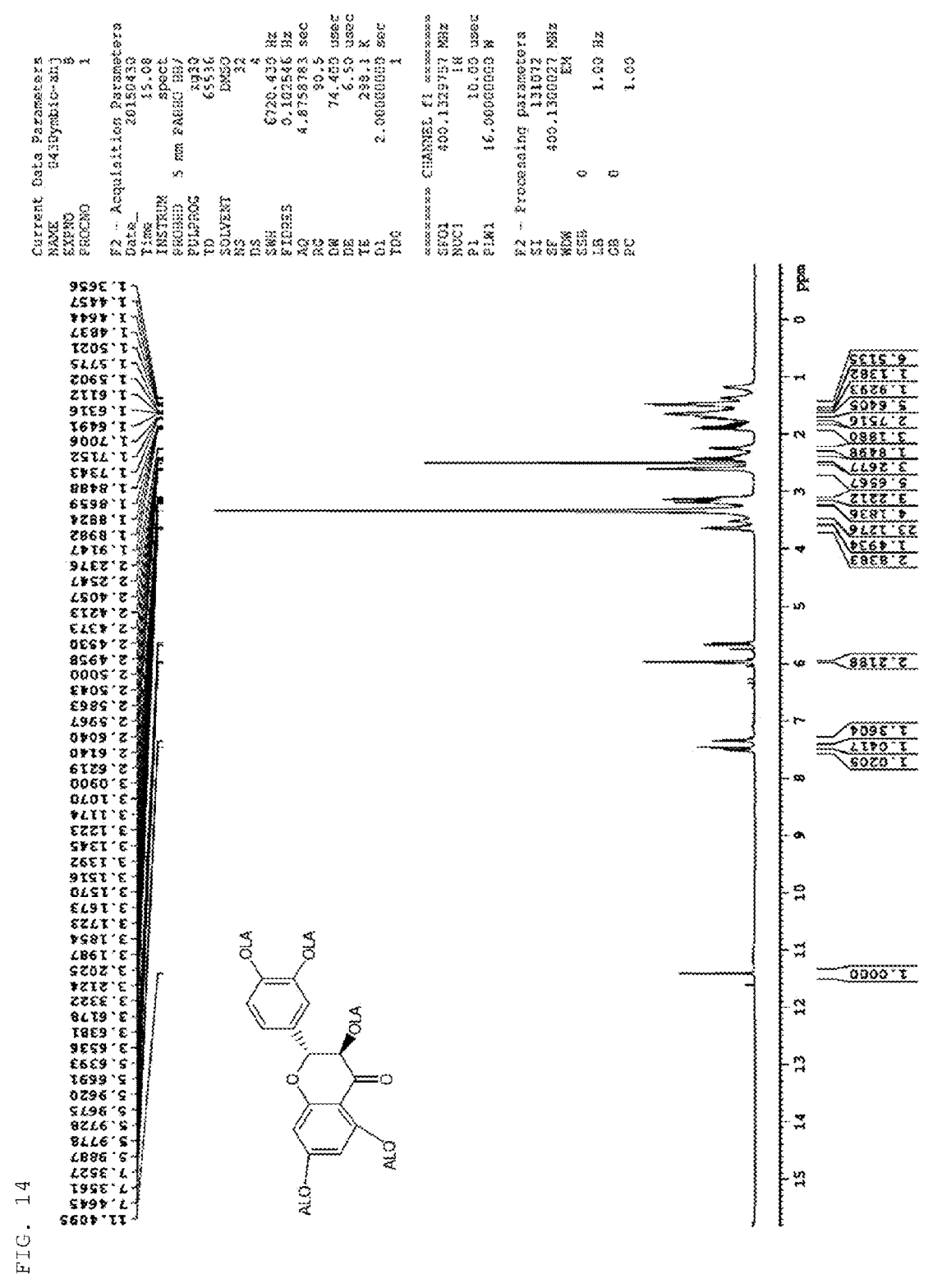

Taxifolin (0.48 g, 1.58 mmol) was dissolved in anhydrous dioxane (17 ml). The previously prepared lipoyl chloride (1.99 g, 8.85 mmol) was added to the solution and the resulting mixture was then stirred at room temperature for 7 minutes. After addition of pyridine (0.71 ml, 8.85 mmol), the resulting mixture was stirred at room temperature for 4 hours and was then stood for about 15 hours. After filtration, the resulting filtrate was concentrated under reduced pressure. The concentrate was dissolved in ethyl acetate and then washed with a NaHCO₃ (3%) solution and distilled water. The ethyl acetate layer was concentrated under reduced pressure. As a result, 2-(3,4-bis(5-(1,2-dithiolan-3-yl)pentanoyloxy)phenyl)-4-oxochroman-3,5,7-triyl tris(5-(1,2-dithiolan-3-yl)pentanoate) (1.8 g) was obtained. FIG. 14 shows NMR results of synthesized 2-(3,4-bis(5-(1,2-dithiolan-3-yl)pentanoyloxy)phenyl)-4-oxochroman-3,5,7-triyl tris(5-(1,2-dithiolan-3-yl)pentanoate).

Figure 15:
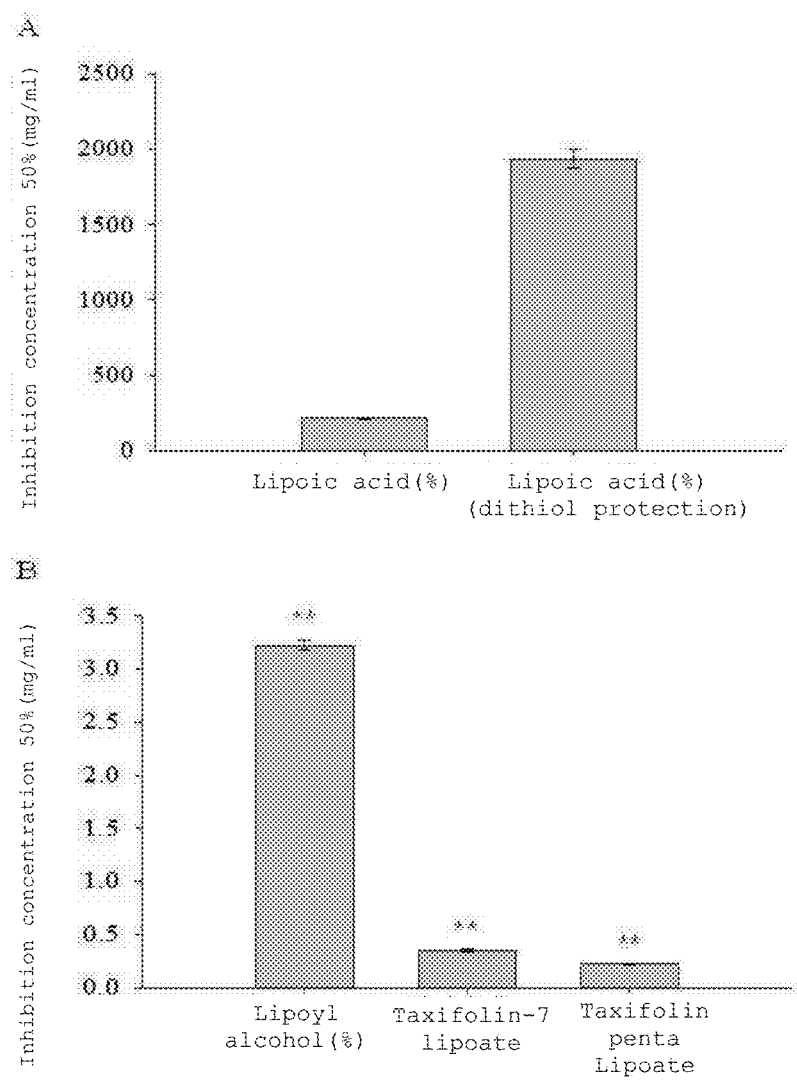
FIG. 15 shows DPPH radical scavenging activities of taxifolin derivatives synthesized in Examples 1 and 2.

Test Example 1: Measurement of Antioxidant Capacity of Synthesized Taxifolin Derivative (1) DPPH Assay The antioxidant effect of synthesized taxifolin derivative was measured using a DPPH(1,1-diphenyl-2-picrylhydrazyl) radical (Blois M S. 1958. Antioxidant determination by the use of a stable free radical. Nature 25: 1199-1120). For measurement, different concentrations of 0.1 mL of the synthesized taxifolin derivatives were prepared and then mixed with 2.5 mL of ethanol. 0.5 mL of a 0.2 mM DPPH solution was added to the resulting mixture and reacted in the dark for one hour. Then, the absorbance of the reaction product was measured at 517 nm using a UV/Vis-spectrophotometer (BIO-RAD, USA). All tests were repeated three times, methanol was used as a blank sample and DPPH radical effect was calculated in accordance with the following Equation 1. DPPH radical scavenging activity was represented by $IC_{50}$ (the concentration required for 50% inhibition).

$$\text{Scavenging effect (\%)}=(A-B)/A\times 100 \qquad \text{[Equation 1]}$$

where A=absorbance at 517 nm without test sample
where B=absorbance at 517 nm with test sample $IC_{50}$ of the respective samples are shown in FIGS. 15A and 15B. FIG. 15 shows DPPH radical scavenging activities of taxifolin derivatives synthesized in Examples 1 and 2 {(**)p<0.05, (*)p<0.5}. As can be seen from FIG. 15A, lipoic acid exhibited $IC_{50}$ of about 250 mg/ml and lipoic acid (dithiol protection) exhibited $IC_{50}$ of about 2,000 mg/ml. However, as can be seen from FIG. 15B, the taxifolin derivatives of Examples 1 and 2 synthesized according to the present invention exhibited very low $IC_{50}$. Taxifolin pentalipoate exhibited $IC_{50}$ of 0.22±0.003 mg/ml and taxifolin-7 lipoate exhibited $IC_{50}$ of 0.34±0.009 mg/ml. Respective $IC_{50}$ values are shown in Table 1 below.

TABLE 1

| Layer | Antioxidative activity ($IC_{50}$ mg/mL) |
| --- | --- |
| Lipoic acid | 515.77 ± 5.41 |
| Lipoic acid (dithiol protection) | 1936.36 ± 61.76 |
| Lipoic alcohol | 3.22 ± 0.05 |
| Taxifolin-7 lipoate | 0.34 ± 0.009 |
| Taxifolin penta lipoate | 0.22 ± 0.003 |

(2) FRAP Assay

FRAP assay of the samples was conducted by slightly modifying the method of Benzie and Strain (Benzie I F F, Strain J J. 1996. The ferric reducing ability of plasma (FRAP) as a measure of "Antioxidant power": The FRAP assay. Anal Biochem 230: 70-79). The FRAP reagent was prepared by heating 25 mL acetate buffer (300 mM, pH 3.6) at 37' C and adding a solution of 5 mL of 10 mM 2,4,6-tris (2-pyridyl)-s-triazine (TPTZ, Sigma) and 2.5 mL of 20 mM ferric sulfate ($FeSO_4$) in 40 mM HCl thereto. 0.03 mL of the sample (Example 1 or Example 2) and 0.09 mL of distilled water were added to 0.9 mL of the prepared FRAP reagent, reaction was proceeded at 37° C. for 10 minutes and absorbance at 593 nm was measured using a spectrophotometer (Benchmark PLUS Bio-Rad). Distilled water, instead of the sample, was used as the blank. 1 mg/mL of ascorbic acid was used as a control group. A calibration equation for $FeSO_4$ made by repetition at different concentrations of 0.125, 0.25, 0.5, 1 and 2 mM was obtained and measurement values of the samples were converted to FRAP values by applying the measurement values thereto. All measurements were repeated three times.

Figure 16:
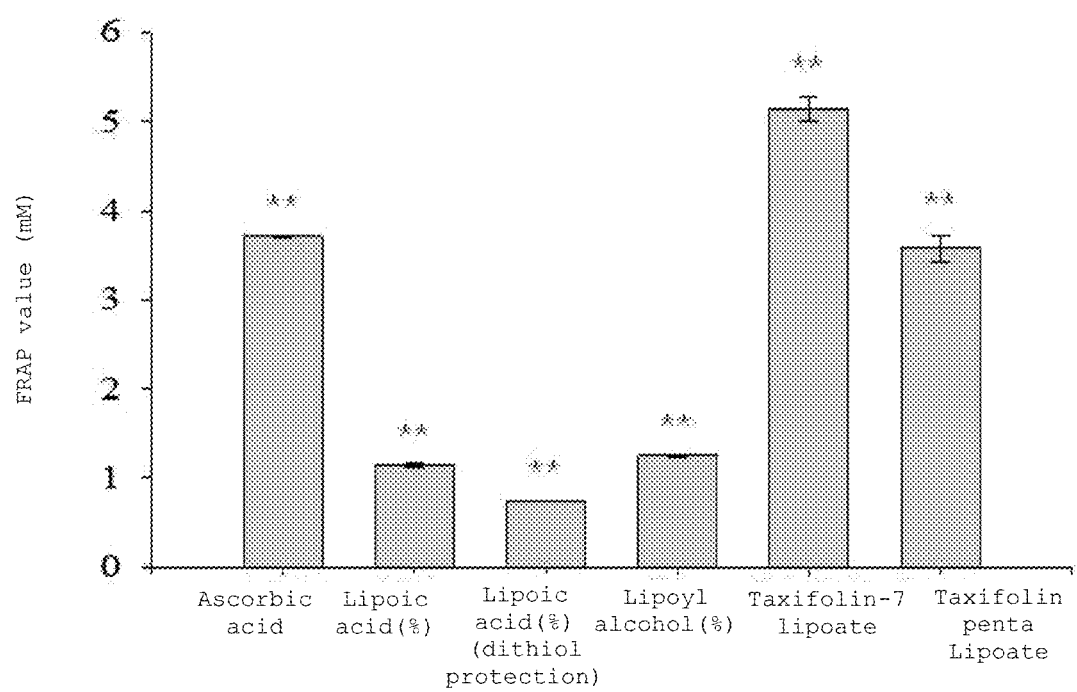
FIG. 16 shows FRAP assay results of taxifolin derivatives synthesized in Examples 1 and 2.

Test results are shown in FIG. 16. FIG. 16 shows FRAP assay results of taxifolin derivatives synthesized in Examples 1 and 2 {(**)p<0.05, (*)p<0.5}. Taxifolin-7 lipoate had the highest value and taxifolin penta lipoate had the next highest value. Respective FRAP values are shown in Table 2 below.

TABLE 2

| Layer | FRAP value (mM) |
| --- | --- |
| Ascorbic acid | 3.7 ± 0.007 |
| Lipoic acid | 1.14 ± 0.019 |
| Lipoic acid (dithiol protection) | 0.74 ± 0.006 |
| Lipoic alcohol | 1.24 ± 0.007 |
| Taxifolin-7 lipoate | 5.14 ± 0.138 |
| Taxifolin penta lipoate | 3.57 ± 0.146 |

As apparent from the above description, in accordance with the method, taxifolin derivatives having higher antioxidant activity than taxifolin can be synthesized using lipoic acid. As such, a novel taxifolin derivative synthesized according to the present invention can exhibit anti-aging effects when used for cosmetics and the like.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A compound represented by the following Formula 8 of 7-(5-(1,2-dithiolan-3-yl)pentyloxy)-2-(3,4-dihydroxyphenyl)-3,5-dihydroxychroman-4-one:

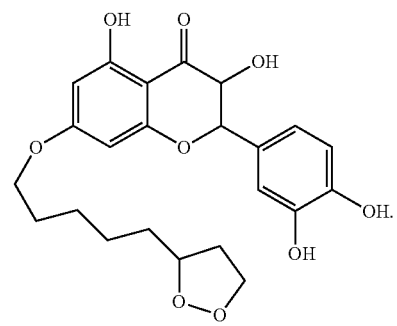

[Formula 8]

2. A compound represented by the following Formula 10 of 2-(3,4-bis(5-(1,2-dithiolan-3-yl)pentanoyloxy)phenyl)-4-oxochroman-3,5,7-triyl tris(5-(1,2-dithiolan-3-yl)pentanoate):

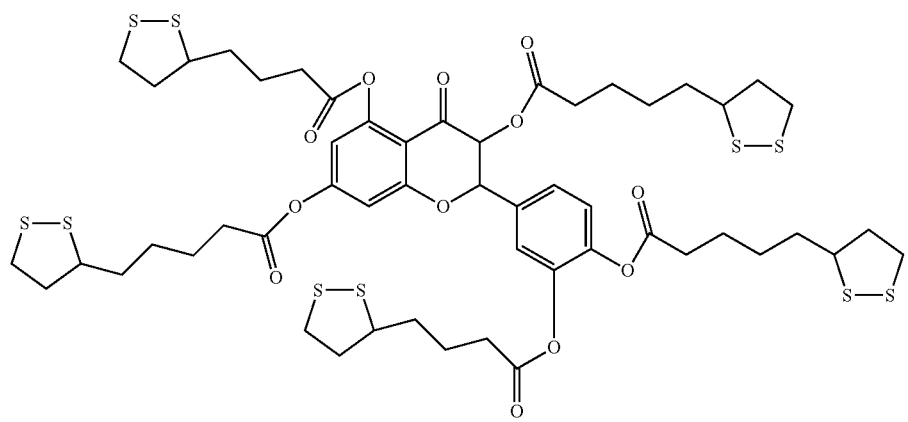

[Formula 10]

3. A cosmetic composition comprising the 7-(5-(1,2-dithiolan-3-yl)pentyloxy)-2-(3,4-dihydroxyphenyl)-3,5-dihydroxychroman-4-one according to claim 1.

4. A cosmetic composition comprising the 2-(3,4-bis(5-(1,2-dithiolan-3-yl)pentanoyloxy)phenyl)-4-oxochroman-3,5,7-triyl tris(5-(1,2-dithiolan-3-yl)pentanoate) according to claim 2.

5. A method of synthesizing a compound represented by the following Formula 8 of 7-(5-(1,2-dithiolan-3-yl)pentyloxy)-2-(3,4-dihydroxyphenyl)-3,5-dihydroxychroman-4-one comprising reacting 5-(2,2-dimethyl-1,3-dithian-4-yl)pentyl 2,2,2-trichloroacetimidate having the structure of the following Formula 4 with 4-(3,5-diacetoxy-7-hydroxy-4-oxochroman-2-yl)-1,2-phenylene diacetate having the structure of following Formula 6:

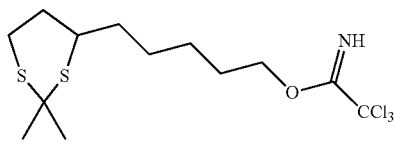

[Formula 4]

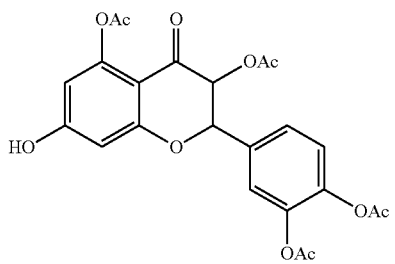

[Formula 6]

6. The method according to claim 5, wherein the 5-(2,2-dimethyl-1,3-dithian-4-yl)pentyl 2,2,2-trichloroacetimidate5-(2,2-dimethyl-1,3-dithian-4-yl)pentyl 2,2,2-trichloroacetimidate is synthesized from lipoic acid as a starting material.

7. The method according to claim 5, wherein the 4-(3,5-diacetoxy-7-hydroxy-4-oxochroman-2-yl)-1,2-phenylene diacetate is synthesized from taxifolin as a starting material.

8. A method of synthesizing taxifolin penta lipoate having the structure represented by the following Formula 10 of 2-(3,4-bis(5-(1,2-dithiolan-3-yl)pentanoyloxy)phenyl)-4-oxochroman-3,5,7-triyl tris(5-(1,2-dithiolan-3-yl)pentanoate) comprising reacting 5-(1,2-dithiolan-3-yl)pentanoyl chloride having the structure of Formula 9 with taxifolin:

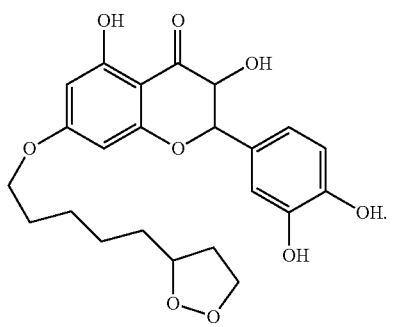

[Formula 8]

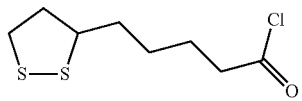

[Formula 9]

[Formula 10]

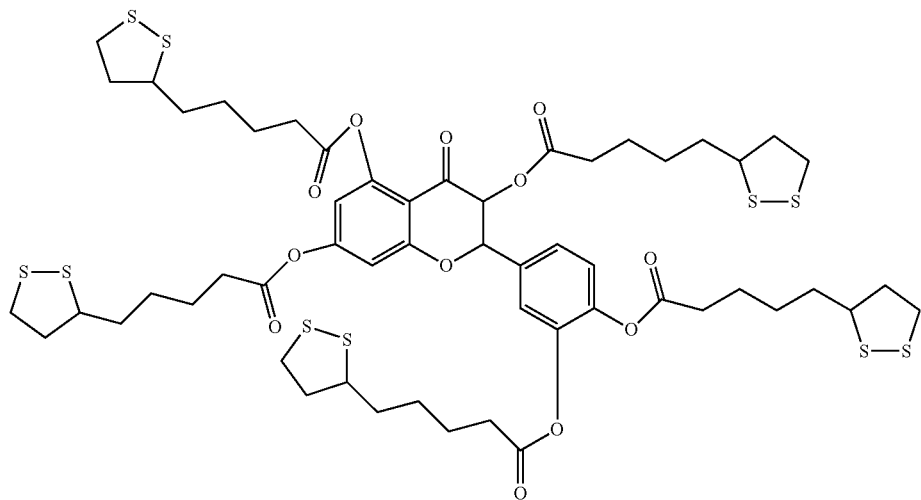

9. The method according to claim 8, wherein the 5-(1,2-dithiolan-3-yl)pentanoyl chloride is synthesized from lipoic acid as a starting material.

10. A method of reducing skin oxidation comprising applying the composition of claim 3 to the skin of a subject in need thereof.

11. A method of reducing skin oxidation comprising applying the composition of claim 4 to the skin of a subject in need thereof.

* * * * *